(12) United States Patent
Acosta Alba et al.

(10) Patent No.: US 9,549,978 B2
(45) Date of Patent: Jan. 24, 2017

(54) AMINO ACID SEQUENCES FOR CONTROLLING PATHOGENS

(71) Applicants: Jannel Acosta Alba, La Habana (CU); Mario Pablo Estrada Garcia, La Habana (CU)

(72) Inventors: Jannel Acosta Alba, La Habana (CU); Mario Pablo Estrada Garcia, La Habana (CU)

(73) Assignee: CENTRO DE INGENIERIA GENETICA Y BIOTECHNOLOGIA, La Habana (CU)

( * ) Notice: Subject to any disclaimer, the term of this patent is extended or adjusted under 35 U.S.C. 154(b) by 0 days.

(21) Appl. No.: 14/346,562

(22) PCT Filed: Oct. 1, 2012

(86) PCT No.: PCT/CU2012/000005
§ 371 (c)(1),
(2) Date: Mar. 21, 2014

(87) PCT Pub. No.: WO2013/044890
PCT Pub. Date: Apr. 4, 2013

(65) Prior Publication Data
US 2014/0294871 A1  Oct. 2, 2014

(30) Foreign Application Priority Data
Sep. 30, 2011  (CU) .................. 2011-0181

(51) Int. Cl.
*C07K 14/47* (2006.01)
*A61K 39/39* (2006.01)
(Continued)

(52) U.S. Cl.
CPC ............. *A61K 39/39* (2013.01); *A23K 20/147* (2016.05); *C07K 14/461* (2013.01); *A61K 38/00* (2013.01)

(58) Field of Classification Search
CPC ........................................................ A61K 38/54
(Continued)

(56) References Cited

U.S. PATENT DOCUMENTS 8,389,679 B2 * 3/2013 Eckert ................ A01N 25/10
424/134.1
8,754,039 B2 * 6/2014 Eckert ................... A61K 8/64
514/2.4
(Continued)

FOREIGN PATENT DOCUMENTS

TW  200825098  6/2008
WO  02/14345  * 2/2002
(Continued)

OTHER PUBLICATIONS

Silphaduang, U et al, Dis. Aquat. Org. 2006, vol. 72, pp. 241-252, Evidence for widespread distribution of piscidin antimicrobial peptids in teleost fish.*
(Continued)

*Primary Examiner* — Albert Navarro
*Assistant Examiner* — Ginny Portner
(74) *Attorney, Agent, or Firm* — Hoffmann & Baron, LLP

(57) ABSTRACT

The present invention relates to antimicrobial peptides, isolated and purified from extracts of tilapia (*Oreochromis niloticus*) gills. Such peptides may be produced by chemical synthesis or by expression in heterologous systems, such as bacteria and yeasts, by conventional molecular biology techniques. These peptides show antimicrobial activity against various organisms, including Gram positive bacteria, Gram negative bacteria, fungi and viruses. The invention also includes compositions for controlling pathogens comprising these antimicrobial peptides. The use of such peptides in vaccine preparations, as molecular adjuvants, is also part of the invention.

12 Claims, 4 Drawing Sheets

(51) Int. Cl.
  *C07K 14/46* (2006.01)
  *A61K 38/00* (2006.01)

(58) Field of Classification Search
  USPC .............................. 530/350; 424/442, 94.2
  See application file for complete search history.

(56) References Cited

U.S. PATENT DOCUMENTS

| | | | | |
|---|---|---|---|---|
| 2003/0056244 A1* | 3/2003 | Huang | ................... | B82Y 30/00 800/278 |
| 2003/0083247 A1* | 5/2003 | Noga | ................... | C07K 14/461 514/44 R |
| 2003/0105281 A1* | 6/2003 | Noga | ................... | C07K 14/461 530/350 |
| 2006/0093596 A1* | 5/2006 | Douglas | ............... | C07K 14/461 424/94.2 |
| 2013/0336955 A1* | 12/2013 | Bakar | ................ | C07K 14/4723 424/94.61 |

FOREIGN PATENT DOCUMENTS

| | | | | |
|---|---|---|---|---|
| WO | 2004/018706 | * | 3/2004 | ............... C12Q 1/68 |
| WO | 2009/149554 | * | 12/2009 | ............... C07K 7/08 |

OTHER PUBLICATIONS

Corrales, J et al Developmental and Comparative Immunology, 2009, pp. 1-13, Detection of antimicrobial peptides related to piscidin 4 in important aquacultured fish.*
Lee, Sung-Ah et al, Biochemistry, 2007, vol. 46, pp. 3653-3663, Solution Structure and Cell Selectivity of Piscidin 1 and Its analogues.*
Peng, Kuan-Chieh et al, PLoS ONE vol. 7(11) e50263; pp. 1-12, Five Different Piscidins from Nile Tilapia, Oreochromis niloticus:Analysis of Their Expressions and Biological Functions.*
Park, N. G. e tal, Biochemistry, 2011, vol. 50, pp. 3288-3299, Structure-Activity Relationships of Piscidin4, a Piscine Antimicrobial Peptide.*
Silphaduang, U et al, Dis. Aquat Org 2006, vol. 72, pp. 241-252.*
Ellis, Ronald W, Ph.D, 575Vaccines, 1988, Chapter 29, New Technologies for Making Vaccines, pp. 568-575, Plotkin & Mortimer Publishers.*
Boslego, John W. et al, Vaccines and Immunotherapy, 1991, Chapter 17, pp. 211-223, Gonorrhea Vaccines.*
Bellamy et al, "Antibacterial spectrum of lactoferricin B, a potent bactericidal peptide derived from the N-terminal region of bovine lactoferrin", Journal of Applied Bacteriology, vol. 73, pp. 472-479, Zama City, Japan, 1992.
Zanetti et al, "Cathelicidins: a novel protein family with a common proregion and a variable C-terminal antimicrobial domain", Federation of European Biochemical Societies, Letters, vol. 274, pp. 1-5, Trieste, Italy, 1995.
Boman, "Innate immunity and the normal microflora", Immunological Reviews, vol. 173, pp. 5-16, Denmark, 2000.
Zasloff, "Antimicrobial peptides of multicellular organisms", Nature Reviews, vol. 415, Washington, DC, 2002.
Shai, "Mode of Action of Membrane Active Antimicrobial Peptides", Biopolymers (Peptide Science), vol. 66, pp. 236-248, Israel, 2002.
Brogden, "Antimicrobial Peptides: Pore Formers or Metabolic Inhibitors in Bacteria?", Nature Reviews, Microbiology, vol. 3, pp. 238-250, Iowa, 2005.
Jelinek et al, "Membrane Interactions of Host-defense Peptides Studied in Model Systems," Current Protein and Peptide Science, vol. 6, pp. 103-114, Israel, 2005.
Campagna et al, "Structure and Mechanism of Action of the Antimicrobial Peptide Piscidin", Biochemistry, vol. 46, pp. 1771-1778, France, 2007.
Subramanian et al, "Comparison of the biochemical composition of normal epidermal mucus and extruded slime of hagfish (*Myxine glutinosa* L.)", Fish & Shellfish Immunology, vol. 25, pp. 625-632, Canada, 2008.
Magnadottir, "Immunological Control of Fish Diseases", Mar Biotechnol, vol. 12, pp. 361-379, Iceland, 2010.
Noga et al, "Application of antimicrobial polypeptide host defenses to aquaculture: Exploitation of downregulation and upregulation responses", Comparative Biochemistry and Physiology, Part D, vol. 6, pp. 44-54, Norway, 2011.
Carpio et al, "Novel gene isolated from *Caligus rogercresseyi*: a promising target for vaccine development against sea lice", Vaccine, vol. 29, pp. 2810-2820, 2011.

* cited by examiner

SEQUENCE LISTING

```
<160> NUMBER OF SEQ ID NOS: 6

<210> SEQ ID NO 1
<211> LENGTH: 23
<212> TYPE: PRT
<213> ORGANISM: Oreochromis niloticus

<400> SEQUENCE: 1

Phe Ile His His Ile Ile Gly Gly Leu Phe Ser Val Gly Lys His Ile
 1               5                  10                  15

His Gly Leu Ile His Gly His
            20

<210> SEQ ID NO 2
<211> LENGTH: 25
<212> TYPE: PRT
<213> ORGANISM: Oreochromis niloticus

<400> SEQUENCE: 2

Phe Ile His His Ile Ile Gly Gly Leu Phe Ser Ala Gly Lys Ala Ile
 1               5                  10                  15

His Arg Leu Ile Arg Arg Arg Arg Arg
            20                  25

<210> SEQ ID NO 3
<211> LENGTH: 32
<212> TYPE: PRT
<213> ORGANISM: Oreochromis niloticus

<400> SEQUENCE: 3

Ile Trp Asp Ala Ile Phe His Gly Ala Lys His Phe Leu His Arg Leu
 1               5                  10                  15

Val Asn Pro Gly Gly Lys Asp Ala Val Lys Asp Val Gln Gln Lys Gln
            20                  25                  30

<210> SEQ ID NO 4
<211> LENGTH: 69
<212> TYPE: DNA
<213> ORGANISM: Oreochromis niloticus

<400> SEQUENCE: 4
tttattcacc atattatcgg tggactgttt agtgttggca aacatatcca cggcctcatc      60
cacggacat                                                             69

<210> SEQ ID NO 5
<211> LENGTH: 75
<212> TYPE: DNA
<213> ORGANISM: Oreochromis niloticus

<400> SEQUENCE: 5
tttattcacc atattatcgg tggactgttt agtgctggca aggctatcca tcgcctcata      60
cgacgtagac gaaga                                                      75

<210> SEQ ID NO 6
<211> LENGTH: 96
<212> TYPE: DNA
```

```
<213> ORGANISM: Oreochromis niloticus

<400> SEQUENCE: 6
atttgggacg caattttcca tggagccaaa cattttcttc atcggctcgt caatcctggt    60
ggcaaggatg ctgtcaagga tgtccaacaa aagcaa                              96
```

US 9,549,978 B2

AMINO ACID SEQUENCES FOR CONTROLLING PATHOGENS

This application is the U.S. National Phase of, and Applicants claim priority from, International Application No. PCT/CU2012/000005 filed 1 Oct. 2012, and Cuban Patent Application No. 2011-0181, filed 30 Sep. 2011, each of which are incorporated herein by reference.

INCORPORATION OF SEQUENCE LISTING

Incorporated herein by reference in its entirety is the Sequence Listing for the above-identified Application. The Sequence Listing is disclosed on a computer-readable ASCII text file titled "Sequence_Listing_976_88PCTUS.txt", created on Mar. 21, 2014. The sequence.txt file is 2 KB in size.

TECHNICAL FIELD

The present invention is related to the field of biotechnology, specifically with the obtainment of antimicrobial peptides and their use for the control of pathogens. When the antimicrobial peptides are applied, they effectively achieve the control of diseases caused by pathogens. Furthermore, these peptides contribute to enhance the immune response induced by various antigens included in the vaccines.

PRIOR ART

Fish have a powerful innate immune system that acts as a first line of defense against a wide spectrum of pathogens (Subramanian et al. (2008) Fish and Shellfish Immunol. 25:625-632), and an adaptive immune system poorly developed (Magnadottir, (2010) Mar Biotechnol. 12:361-379). One of the ways in which the fish fight pathogens is by secretion of antimicrobial peptides (AMP) as an innate defense mechanism. The AMPs have a fundamental role in the innate immune system and protect against a variety of bacteria, fungi, viruses and other pathogens causing infections (Solomon, (2008) Lancet Neurol. 7:116-118). In general, AMPs are secreted in saliva, mucus, circulatory system and other areas that are targets for pathogens (Noga et al. (2010) Comp Biochem Physiol D: Genom Proteom. 6:44-54). The AMPs are divided into five categories, based on their amino acid composition and structure. In these categories are included anionic peptides, linear peptides with α-helical amphipathic structure, cationic peptides enriched with specific amino acids, peptide fragments and peptide with cysteines that form intramolecular bonds (Brogden (2005) Nat Rev Microbiol. 3:238-50; Boman (2000) Immunol Rev.173:5-16). Anionic peptides are produced in millimolar concentrations, requiring the zinc as a cofactor, and show antimicrobial activity against Gram-positive bacteria and Gram-negative bacteria. The linear and cationic peptides with amphipathic α-helix structure have less than 40 amino acids and possess a three-dimensional structure with a hinge region in the middle portion. While its structure is disordered in solution, these molecules adopt a secondary α-helix structure when they are in contact with the membranes (Brogden (2005) Nat Rev Microbiol. 3:238-50). The other group, that consists of linear cationic peptides enriched with specific amino acids, do not have cysteine residues, therefore these peptides have a very flexible structure in solution (Brogden (2005) Nat Rev Microbiol. 3:238-50). The fourth group comprises charged peptides, which are fragments from larger proteins. These peptides possess antimicrobial activity and structure similar to the other groups of peptides (Bellamy et al. (1992) J Appl Bacteriol. 73:472-9; Zanetti et al. (1995) FEBS Lett. 374:1-5). The fifth group of peptides consists of approximately 380 members, which contain six conserved cysteine residues that form intramolecular bonds and a β sheet structure (Brogden (2005) Nat Rev Microbiol. 3:238-50). This group comprises defensins and hepcidin (Boman et al. (2000) Immunol Rev. 173:5-16).

While AMPs are commonly classified by variations in structural characteristics, there are some features that are common to most of these peptides. For example, they generally have less than 60 amino acids, have a broad spectrum of antimicrobial activity under physiological conditions, and have a positive charge (Zasloff (2002) Nature 415:389-395). Most amphipathic AMPs adopt a structure that contributes to the mechanism of action of these peptides, based on its interaction with the lipid cell membrane of pathogens such as bacteria and enveloped viruses (Shai (2002) Biopolymers 66: 236-48; Jelinek and Kolusheva (2005) Curr. Protein Pept. Sci. 6: 103-14). This interaction causes rapid destabilization/permeabilization of the pathogen lipid membrane. Several observations suggest that besides the mechanism of pore formation, the AMPs can inhibit the synthesis of cell wall, nucleic acids and proteins and even inhibit the enzyme activity (Brogden et al. (2005) Nat. Immunol. 6: 558-64; Campagna et al. (2007) Biochemistry 46: 1771-8).

Because of the ability of microorganisms to develop resistance to antibiotics, and the presence of diseases caused by pathogens for which there are no adequate treatments, it is necessary to search for new molecules with antimicrobial activity. Therefore, an important problem to solve is to develop new antimicrobial products, specially proteins and/or peptides, able to efficiently control a wide range of pathogens and that also have an impact on the innate and adaptive immunity, aspects of great importance in human and veterinary medicine, including aquaculture.

DETAILED DESCRIPTION OF THE INVENTION

The present invention solves the above mentioned problem by providing a new alternative for the control and treatment of infections produced by pathogens, including those caused by bacteria, viruses or fungi. In the present invention are reported, for the first time, the antimicrobial peptides identified as SEQ ID No. 1,2 and 3. It is also an object of the invention the amino acid sequences that comprise in their amino acid sequence those identified as SEQ ID No.1, 2 and 3, or an amino acid sequence with at least 80% identity with the peptides identified as SEQ ID No. 1, 2 or 3.

Three peptides were isolated and sequenced from tilapia (*Oreochromis niloticus*) gill protein extracts, which were called Oreochromicin I, Oreochromicin II and Oreochromicin III. These peptides have not been reported in the literature and are denoted in the invention as SEQ ID No. 1, 2 and 3. These peptides possess antimicrobial effect against Gram-positive bacteria, Gram-negative bacteria, virus and fungi. The peptides of the present invention can be obtained by isolation from its natural source. Besides, the peptides may be obtained by chemical synthesis or by recombinant deoxyribonucleic acid (DNA) technology.

In one embodiment of the invention, the antimicrobial peptides are obtained by recombinant expression in bacteria, yeasts or cells of higher organisms. These antimicrobial peptides can be expressed in different host systems, and isolated from them. In a particular embodiment, the antimicrobial peptides can be expressed in yeast. In a preferred embodiment, the expression by recombinant DNA technology is carried out in *Pichia pastoris*, preferably in the culture supernatant. The antimicrobial peptides of the invention may also be expressed in bacteria. In another preferred embodiment, the expression by recombinant DNA technology is carried out in Escherichia coli. The peptides of the invention may be obtained by protein isolation techniques, from the host, which are widely known by those skilled in this technical field, such as chromatographic techniques, washed pellets, and others.

The use of antimicrobial peptides offers advantages in comparison with other antimicrobial agents, because they have small size (~5 kDa), so are better absorbed through the skin and mucous of aquatic organisms when applied by immersion, which is the administration route with an advantageous cost for aquaculture, and with low levels of pollution. Another advantage is that the antimicrobial peptides stimulate the innate and adaptive immune activity, and increase the resistance to infections by pathogenic agents.

Taking into account the amino acid sequence of each peptide, degenerated oligonucleotides were designed to amplify, by polymerase chain reaction (PCR), the nucleotide sequence encoding each mature peptide. Therefore, another object of this invention is a nucleic acid that comprises a nucleic acid sequence selected from the group consisting of SEQ ID No. 4, SEQ ID No. 5 and SEQ ID No. 6.

Another object of the present invention is a nucleic acid encoding the peptides comprising the amino acid sequences identified as SEQ ID No. 1, 2 and 3, or an amino acid sequence with at least 80% identity with the peptides identified as SEQ ID No. 1, 2 or 3.

The invention also provides a composition for the control of pathogens comprising the peptides identified as SEQ ID No.1, 2 and 3, or peptides with at least 80% identity with the peptides identified as SEQ ID No.1, 2 or 3.

In one embodiment of the invention, the antimicrobial peptides whose sequences are claimed (and the compositions that comprise them) may be used to control a wide variety of pathogens, such as bacterial pathogens (*Aeromonas, Pseudomonas, Corynebacteria, Enterobacteria, Haemophilus, Mycobacteria, Nocardia, Myxobacteria, Streptomyces* and *Vibrio*, among others); viral pathogens (infectious hematopoietic necrosis virus, infectious pancreatic necrosis virus, hemorrhagic septicemia virus, iridovirus, carp hemorrhagic virus, spring viremia of carp virus, *Hirame rhabdovirus* or Snakehead rhabdovirus, lymphocystis virus, infectious salmon anemia, among others), fungi and oomycete (*Saprolegnia, Achlya, Ychthyosporidium hoferi*, among others).

In one embodiment of the invention, the peptides Oreochromicin I, Oreochromicin II and Oreochromicin III, as well as peptides having at least 80% sequence identity with them, are formulated into compositions which are used to control pathogens in different organisms, including mammals and aquatic organisms. Such compositions are administered both preventively and therapeutically in the control of pathogens. The routes of administration include all those that are used for the administration of drugs in humans, and for medicines or additives in the case of animals, which are well known to those skilled in this technical field. In one embodiment, the compositions for the control of pathogens, of the invention, are administered orally, parenterally, or by immersion baths.

It is also an aspect of the invention, the use of a peptide comprising an amino acid sequence selected from the group consisting of SEQ ID No. 1, SEQ ID No. 2 and SEQ ID No. 3, or an amino acid sequence with at least 80% identity with SEQ ID No. 1, SEQ ID No. 2 or SEQ ID No. 3 for the manufacture of a composition for the control of pathogens.

Another aspect thereof is to provide a method for controlling pathogens that attack several organisms, characterized by the administration of an effective amount of a peptide comprising an amino acid sequence selected from the group consisting of SEQ ID No. 1, SEQ ID No. 2 and SEQ ID No. 3, or an amino acid sequence with at least 80% identity with SEQ ID No. 1, SEQ ID No. 2 or SEQ ID No. 3 to said organisms.

In a particular embodiment, the peptides of the invention are applied to fish by periodic injections, at concentrations between 0.1 and 10 µg/fish; by immersion baths at intervals of 1-15 days (on consecutive or alternate days) in fresh water or sea water, at a peptide concentration between 0.01 and 0.1 mg/L of water. Also the peptides could be applied as a feed additive for fish, at a concentration of about 50-750 µg of peptide/kg of feed. In all cases, a significant increase in resistance to diseases caused by pathogens, such as viruses, bacteria or fungi among others, are obtained.

Additionally, this invention provides peptides which are useful as molecular adjuvants for vaccines. In the context of this invention the term "molecular adjuvant" refers to a proteinaceous molecule capable of modulating the immune response to a vaccine antigen, producing an increase in the immune response.

Therefore, the invention also provides a vaccine composition that comprises a peptide comprising an amino acid sequence selected from the group consisting of SEQ ID No. 1, SEQ ID No. 2 and SEQ ID No. 3, or an amino acids sequence with at least 80% identity with SEQ ID No. 1, SEQ ID No. 2 or SEQ ID No. 3, as a molecular adjuvant, and a vaccine antigen.

Another aspect of the invention is to provide a method for increasing the immune response to a vaccine antigen that employs a peptide comprising an amino acid sequence selected from the group consisting of SEQ ID No. 1, SEQ ID No. 2 and SEQ ID No. 3, or an amino acid sequence with at least 80% identity with SEQ ID No. 1, SEQ ID No. 2 or SEQ ID No. 3, as a molecular adjuvant in a vaccine.

EXAMPLES

Example 1

Figure 1:
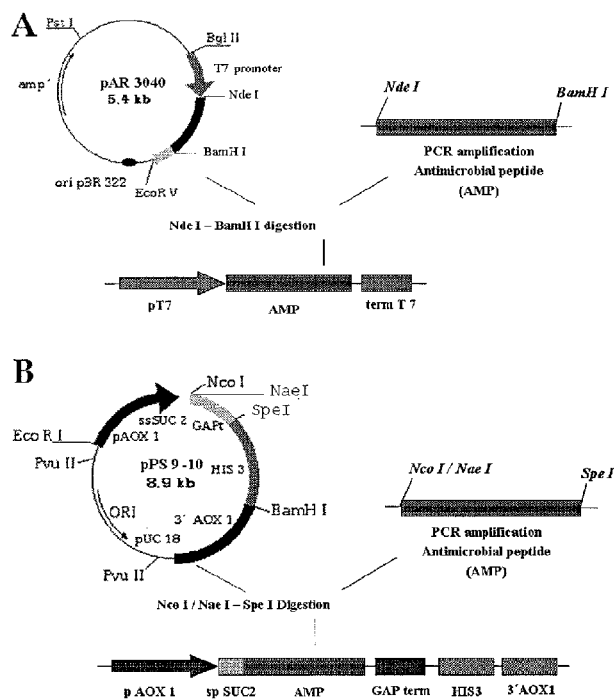
FIG. 1. Cloning strategy of the antimicrobial peptides into the expression vectors for *E. coli* (FIG. 1A) and for the yeast *P. pastoris* (FIG. 1B).

Isolation and Purification of the Antimicrobial Peptides from Tilapia Gills Extracts Tilapia (*Oreochromis niloticus*) gill filaments were macerated in liquid nitrogen and the resulting powder was heated at 100° C. for 10 min and allowed to cool. The extraction of the proteins was performed by adding 150 mL of a solution of HCl 2M, formic acid 10% (v/v), NaCl 2% (w/v) and trichloroacetic acid 1% (v/v), followed by homogenization for 1-2 min. The homogenate was centrifuged at 20 000×g for 30 min, the supernatant was adjusted to pH 4.0 and filtered. The resulting filtrate was used as the acid extract and was applied to a Sep-Pak C18 column (Waters, Milford, Mass., USA). After washing with trifluoroacetic acid 0.1% (v/v), the fraction corresponding to peptides was eluted at 80% acetonitrile/0.1% trifluoroacetic acid. The eluate was dried and dissolved in acetic acid 1M, and adsorbed to a matrix of SP-Sephadex C-25. Successive steps of elutions with acetic acid 1M, pyridine 2M and pyridine 2M/acetic acid (pH 5.0) yielded five fractions. It was performed antimicrobial activity to each fraction and was chosen the fraction 2 for subsequent purification steps.

The selected fraction was lyophilized and dissolved in acetonitrile 40% containing trifluoroacetic acid 0.1%. An aliquot of the solution was applied to a TSKgel G2000SW column (gel filtration, high performance liquid chromatography (HPLC)) and eluted with acetonitrile 40% containing trifluoroacetic acid 0.1%. The same fraction was repeatedly injected into the column, and the resulting fraction with a molecular weight lower than 5 kDa and showing antimicrobial activity was lyophilized and subjected to reversed phase chromatography (RP-HPLC) and mass spectrometry (ESI-MS). The molecular weight of this fraction was determined by gel electrophoresis on Tricine-sodium dodecyl sulfate (16.5% T/3% C) (abbreviated Tricine-SDS-PAGE).

The separation of proteins by HPLC was conducted on a Hewlett-Packard HP1100 system. Solvent A was acetonitrile 5% containing trifluoroacetic acid 0.1% and solvent B was acetonitrile 80% containing trifluoroacetic acid 0.085%. Fraction A was reconstituted with solvent A and subjected to RP-HPLC on a C8-3 column (4.6×150 mm). The gradient was 0-2 min 0% solvent B, 2-5 min 0-20% solvent B, 5-55 min 20-47% solvent B, and 55-80 min 47-100% solvent B. The resulting fractions which show antimicrobial activity were lyophilized, reconstituted in $KH_2PO_4/H_3PO_4$ 5 mM (pH 3.0) containing acetonitrile 25% and loaded onto a PolySulfoethyl Aspartamide column (4.6×200 mm). Fractions were eluted with a linear gradient of KCl. The molecular weights of the fractions that showed the greatest antimicrobial activity were 2527.3, 2981.9 and 3654.6 Da. These peptides were named Oreochromicin I, II and III, respectively. The amino acid sequences of each peptide with antimicrobial activity were determined, and are identified hereafter as SEQ ID No. 1, 2 and 3, respectively. Furthermore, was made sequences analysis using BlastX program and was found that these peptides were not reported previously.

Example 2

Construction of Vectors for the Antimicrobial Peptide Expression, Intracellularly in *E. coli* and Extracellularly in Yeast *P. pastoris*

The complementary DNAs (cDNA) were obtained from ribonucleic acid (RNA) isolated from gills of tilapia (*O. niloticus*) by reverse-transcription reaction. The reactions were carried out following the instructions described in the kit "Reverse Transcription System" (Promega, USA). Briefly, 4 μg of total RNA were placed into a microcentrifuge tube free of nucleases and were incubated for 10 minutes at 70° C. Thereafter it was added the rest of the reaction components (4 µL of 25 mM $MgCl_2$, 2 µL of the mixture of 10 mM deoxynucleotide triphosphates (dNTPs), 2 µL of reverse-transcription 10× buffer, 0.5 µL of ribonuclease inhibitor, 1 µL of oligo (dT) 500 µg/mL, 20 units of reverse-transcriptase and water previously treated with diethyl pyrocarbonate to a final volume of 20 µL). The reaction was incubated for 15 minutes at 42° C. and was stopped at 95° C. for 5 minutes.

The nucleotide sequences encoding for the mature region of the antimicrobial peptides were amplified, from the obtained cDNAs, by PCR, using degenerate synthetic oligonucleotides designed from the amino acid sequence of each peptide. In all cases we obtained a DNA band of the expected size. The bands were purified from agarose gel and inserted into the commercial vector pGEM-TEasy (Promega) for sequencing. The DNA sequences encoding the peptides are identified as SEQ ID No. 4, 5 and 6.

The DNA sequences encoding antimicrobial peptides were inserted into the *E. coli* expression vector pAR 3040 using the restriction sites NdeI/BamHI (FIG. 1A). To amplify the band corresponding to each of peptides, oligonucleotides that recognize specific sequences 5' and 3' ends of each, and have recognition sites of the restriction enzymes which facilitate cloning into the expression vector were used. For each peptide, it was selected one of the recombinant clones to transform the *E. coli* BL21DE3 strain and to induce expression of the gene under the regulation of T7 promoter, using as inductor isopropyl-β-D-1-thiogalactopyranoside (IPTG) 1 mM. The gene expression was carried out at 37° C. for 6 hours. The expression of recombinant peptides was checked by Tricine-SDS-PAGE and ESI-MS.

The pPS9 and pPS10 vectors and specific oligonucleotide that recognize sequences 5' and 3' of each peptide and have recognition sites of restriction enzymes were used to construct the antimicrobial peptides expression vector in *P. pastoris*. For cloning in pPS9 vector were used NcoI and SpeI sites, and for cloning into the pPS10 vector were used NaeI and SpeI sites. These cloning strategies do not add amino acids to the interest protein (FIG. 1B).

The plasmids were linearized before transforming the *P. pastoris* MP36 strain. The transformation was conducted by electroporation. The MP36 strain is an auxotrophic mutant his3 which acquired a His+ phenotype after transformation.

The transformant clones were identified by Dot Blot. Using the Southern Blot technique was determined, in which of these clones, the integration occurred by the replacement of *P. pastoris* gene AOX1 by the expression cassette of recombinant plasmid, which corresponds with a $Mut^s$ phenotype (low usage of methanol) and His+. The yeast *P. pastoris* secretes low levels of self proteins and its culture medium does not need protein supplements, so you can expect a heterologous protein that is secreted to the extracellular medium, constituting a majority of the total protein in the medium (more than one 80%) (Tschopp et al. (1987) Bio/Technology 5:1305-1308).

The peptides expression on *P. pastoris* was carried out in 5 liter by addition of methanol to the culture medium. The expression of recombinant peptides and its integrity were checked by Tricine-SDS-PAGE and ESI-MS.

Example 3

Purification and Biological Activity Assay of the Antimicrobial Peptides

Figure 2:
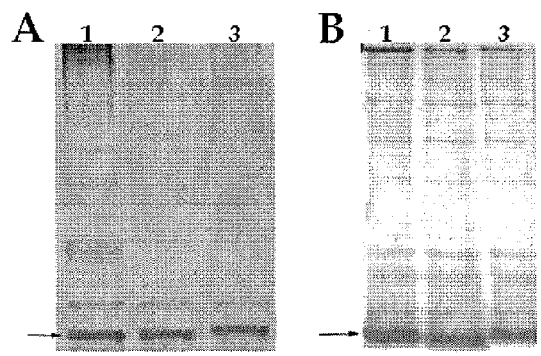
FIG. 2. Purification of the antimicrobial peptides from the *P. pastoris* culture supernatant (FIG. 2A) and from the *E. coli* rupture supernatant (FIG. 2B). Lane 1: Oreochromicin I; Lane 2: Oreochromicin II, Lane 3: Oreochromicin III.

Antimicrobial peptides recombinantly obtained were purified from *E. coli* rupture supernatant or from *P. pastoris* culture supernatant. First, the dialysis was performed in sodium acetate 25 mM (pH 4.5), using a membrane with a pore size of 1 kDa. The product of the dialysis was applied to a resin of cationic exchange CM-Sepharose Fast Flow equilibrated with sodium acetate 25 mM (pH 4.5), and proteins were eluted with sodium chloride 1M, Tris 50 mM (pH 7.6). The fractions containing the peptides were collected and concentrated using an ultrafiltration system using a membrane with a pore size of 1 kDa. For detection, we employed a wavelength of 254 nm. The purification was checked by Tricine-SDS-PAGE and proteins were visualized by Coomassie Blue staining (FIG. 2).

The peptides of the invention were also obtained by chemical synthesis using methods known to those skilled in this technical field. The antimicrobial activity of the peptides was determined by the microdilution method. To determine the minimum inhibitory concentration (MIC), each peptide was serially diluted 1:2. Ten microliters of each diluted peptide were incubated with 90 µL of the bacteria or yeast suspension ($5 \times 10^5$ CFU (colony forming units) per mL) in Mueller Hinton broth (bacteria) or Sabouraund broth (fungi) and incubated for 18 h at 28° C. (for fish pathogens and fungi) or 37° C. (for mammalian pathogens). The MIC is defined as the lowest peptide concentration at which inhibition of bacterial growth occurs. All assays were performed in triplicate, and culture medium (without microorganism) and microorganisms to which no peptide was added were used as controls. The results are shown in Table 1.

TABLE 1

Antimicrobial activity of the peptides Oreochromicin I, Oreochromicin II and Oreochromicin III.

|  | Oreochromicin I | Oreochromicin II | Oreochromicin III |
|---|---|---|---|
| *Staphylococcus aureus* (Gram+) | MIC = 5 µM IC50* = 2.8 | MIC = 5 µM IC50 = 2.02 | Did not inhibit |
| *Bacillus subtilis* (Gram+) | MIC = 3 µM IC50 = 1.37 | MIC = 1.7 µM IC50 = 0.5894 | MIC = 106 µM IC50 = 19.22 |
| *Pseudomonas aeuroginosa* (Gram−) | MIC = 35 µM IC50 = 29.36 | MIC = 6.67 µM IC50 = 3.75 | Did not inhibit |
| *E.coli* (Gram−) | MIC = 6.7 µM IC50 = 2.963 | MIC = 5 µM IC50 = 2.289 | Did not inhibit |
| *A. hydrophila* (Gram−) | Did not inhibit | MIC = 160 µM IC50 = 30.41 | Did not inhibit |
| *Edwardsiella tarda* (Gram−) | MIC = 160 µM IC50 = 11.11 | MIC = 20 µM IC50 = 2.085 | MIC = 160 µM IC50 = 37 |
| *Vibrio* sp. (Gram−) | MIC = 80 µM IC50 = 7.45 | MIC = 15 µM IC50 = 2.5 | MIC = 106 µM IC50 = 67.41 |
| *Candida albicans* (fungus) | MIC = 20 µM IC50 = 10.28 | MIC = 26.7 µM IC50 = 12.92 | MIC = 40 µM IC50 = 14.10 |

*IC50: The peptide concentration that produces 50% of bacterial growth inhibition Example 4

Determination of Resistance to Infection by *Aeromonas hydrophila* in Tilapia Previously Treated with Antimicrobial Peptides Administration of the Peptides by Intraperitoneal Injection We proceeded to evaluate the utility of antimicrobial peptides to enhance disease resistance in vivo. In a first test, we used 130 tilapias (*O. niloticus*) with a body weight of 10 g, which were randomly distributed in 13 experimental groups of ten animals per group. This assay was performed in order to determine the minimum time of treatment required to enhance the survival of fish against challenge with A. hydrophila. Each peptide was administered at a concentration of 1 µg per fish by intraperitoneal injection, for 2, 4, 8 and 15 days. An additional group was placed which PBS was administered as a control. The experimental groups were:

Group 1: PBS.
Group 2: Oreochromicin I administrated for 2 consecutive days.
Group 3: Oreochromicin I administrated for 4 consecutive days.
Group 4: Oreochromicin I administrated for 8 consecutive days.
Group 5: Oreochromicin I administrated for 15 consecutive days.
Group 6: Oreochromicin II administrated for 2 consecutive days.
Group 7: Oreochromicin II administrated for 4 consecutive days.
Group 8: Oreochromicin II administrated for 8 consecutive days.
Group 9: Oreochromicin II administrated for 15 consecutive days.
Group 10: Oreochromicin Ill administrated for 2 consecutive days.
Group 11: Oreochromicin III administrated for 4 consecutive days.
Group 12: Oreochromicin III administrated for 8 consecutive days.
Group 13: Oreochromicin Ill administrated for 15 consecutive days.

After the time of peptide administration, we performed a challenge test by intraperitoneal injection of the median lethal dose (LD50) of A. hydrophila, and mortality was recorded during 7 days. We calculated the relative percent of survival (RPS) as:

RPS (%)=(% mortality controls−% mortality treated)/(% mortality controls)×100

As a result, it was observed that the fish treated with Oreochromicin I and Oreochromicin III for 15 days, had an increase in survival (measured as RPS) of 45% compared to the group receiving PBS. Meanwhile, the group treated with Oreochromicin II for 8 days had an increase in survival (RPS) of 48% compared to the group receiving PBS.

A second test was performed to determine the optimal dose of peptide required to increase the survival of the fish following challenge with A. hydrophila. We used 130 tilapias (O. niloticus), with a body weight of about 10 g, which were randomly distributed in 13 experimental groups of 10 animals each. Each peptide was administered at a concentration of 0.5, 1, 5 and 10 µg per fish for 15 days. The experimental groups were:

Group 1: PBS.
Group 2: Oreochromicin I 0.5 µg/fish.
Group 3: Oreochromicin I 1 µg/fish.
Group 4: Oreochromicin I 5 µg/fish.
Group 5: Oreochromicin I 10 µg/fish.
Group 6: Oreochromicin II 0.5 µg/fish.
Group 7: Oreochromicin II 1 µg/fish.
Group 8: Oreochromicin II 5 µg/fish.
Group 9: Oreochromicin II 10 µg/fish.
Group 10: Oreochromicin III 0.5 µg/fish.
Group 11: Oreochromicin III 1 µg/fish.
Group 12: Oreochromicin III 5 µg/fish.
Group 13: Oreochromicin III 10 µg/fish.

After 15 days of peptide administration, we performed a challenge test by is intraperitoneal injection of the LD50 of A. hydrophila, and mortality was recorded during 7 days. RPS was calculated as described above. At 7 days after challenge all three peptides showed dose-dependent effect and have a RPS between 84% and 88%, compared with the group that received PBS alone, which showed a 10% of survival.

Administration of the Peptides by Immersion Bath

A test was conducted to determine the effect of each peptide administered by immersion baths, on the fish survival following challenge with A. hydrophila. 1300 tilapia (O. niloticus) larvae of 5 days post-hatching were used, which were randomly distributed in 13 experimental groups of 100 larvae each. Each peptide was administered at a concentration of 0.01, 0.05, 0.1 and 0.5 mg of peptide per liter of water for 15 days. The experimental groups were:

Group 1: PBS.
Group 2: Oreochromicin I 0.01 mg/L.
Group 3: Oreochromicin I 0.05 mg/L.
Group 4: Oreochromicin I 0.1 mg/L.
Group 5: Oreochromicin I 0.5 mg/L.
Group 6: Oreochromicin II 0.01 mg/L.
Group 7: Oreochromicin II 0.05 mg/L.
Group 8: Oreochromicin II 0.1 mg/L.
Group 9: Oreochromicin II 0.5 mg/L.
Group 10: Oreochromicin III 0.01 mg/L.
Group 11: Oreochromicin III 0.05 mg/L.
Group 12: Oreochromicin III 0.1 mg/L.
Group 13: Oreochromicin III 0.5 mg/L.

After 15 days of administration of the peptides, we performed a challenge test by administration by immersion bath of the LD50 of A. hydrophila and mortality was recorded during 10 days. RPS was calculated as previously described. At 10 days to after challenge, all three peptides showed dose-dependent effect and an RPS between 76% and 89%, compared with the group that received PBS alone, which showed an 18% survival.

Oral Administration as a Feed Additive

A test was conducted to determine the effect of each peptide orally administered, as is a feed additive, on the survival of the fish following challenge with A. hydrophila. We used 130 tilapias (O. niloticus) with a body weight of about 10 g, which were randomly distributed in 13 experimental groups of 10 animals each. Each peptide was administered at a concentration of 50, 250, 500 and 750 µg/kg of feed for 30 days. The experimental groups were:

Group 1: PBS.
Group 2: Oreochromicin I 50 µg/Kg.
Group 3: Oreochromicin I 250 µg/Kg.
Group 4: Oreochromicin I 500 µg/Kg.
Group 5: Oreochromicin I 750 µg/Kg.
Group 6: Oreochromicina II 50 µg/Kg.
Group 7: Oreochromicina II 250 µg/Kg.
Group 8: Oreochromicina II 500 µg/Kg.
Group 9: Oreochromicina II 750 µg/Kg.
Group 10: Oreochromicina III 50 µg/Kg.
Group 11: Oreochromicina III 250 µg/Kg.
Group 12: Oreochromicina III 500 µ/Kg.
Group 13: Oreochromicina III 750 µ/Kg.

After 30 days of administration of the peptides, we performed a challenge test by the intraperitoneal injection of the LD50 of A. hydrophila, and mortality was recorded during 10 days. RPS was calculated. At 10 days after challenge, all three peptides showed dose-dependent effect and an RPS between 80% and 95%, compared with the group that received PBS alone, which showed a 13% survival.

Example 5

Determination of Resistance to Infection by *Staphylococcus aureus* or *Pseudomonas aeruginosa* in Mice We studied the ability of the antimicrobial peptides Oreochromicin I and Oreochromicin II to protect mice from lethal doses of infection with bacterias *S. aureus* and *P. aeruginosa*. In this assay were used male mice (ICR) of 4 weeks of age and with a body weight of 25 g. Bacteria were grown in tryptone soy broth at 37° C. for 8 h.

The amount of bacteria needed to produce between 90 and 100% of mortality were prepared by diluting the cultures in PBS. The number of viable colonies was estimated based on absorbance at 550 nm and verified by plating serial dilutions of the inoculum. In dependence of the microorganism tested and route of administration, we used a dose of $4.5 \times 10^6$ and $1.4 \times 10^9$ CFU/mouse.

15 mice were infected for each dose and survival was monitored for 7-10 days after infection. In a first test, the mice received 0.5 ml of PBS (negative control) or PBS containing the selected antimicrobial peptide, by intraperitoneal injection, immediately after the intraperitoneal administration of bacteria. In a second test was administered *S. aureus* intravenously. Immediately after the administration of the bacteria, the mice received 0.2 ml of PBS or PBS containing antimicrobial peptides intravenously.

As a result, it was found that the peptides Oreochromicin I and Oreochromicin II, administered intraperitoneally at a dose of 0.5 mg/kg, reduces mortality by *S. aureus* and *P. aeruginosa* from 90-100% in the control group to 5-29% in the groups treated with the peptides.

For intravenous infection with *S. aureus*, and the peptide administration at a dose of 2.5 mg/kg, the mortality was reduced from 90-100% in the control to 18-40% in the groups treated with the peptides.

Example 6

Activity of the Antimicrobial Peptides Against Infection by an Iridovirus

EPC cells (epithelioma papulosum cyprinid) were incubated at 28° C., 5% $CO_2$ and 95% relative humidity, in RPMI-1640 containing 10% fetal bovine serum, 1 mM pyruvate, 2 mM glutamine, 100 U/ml penicillin and 100 µg/ml streptomycin. The antimicrobial peptides of the present invention were amplified by PCR using specific primers that recognize sequences 5' and 3' ends of each, and inserted into the pTargeT vector to generate plasmids pTargeT-Oreochromicin I, pTargeT-Oreochromicin II and pTargeT-Oreochromicina III.

EPC cells were grown to 90% of confluence and transfected transiently, with the vectors containing the genes encoding antimicrobial peptides and with the empty vector pTargeT at a DNA concentration of 1 µg/mL using lipofectamine 2000. The expression of antimicrobial peptides in transfected cells was analyzed by RT-PCR. The PCR products were visualized on 2% agarose gel, stained with ethidium bromide. At 24 hours after transfection, each well was washed 3 times with PBS and treated with various concentrations of Rana grylio virus (RGV). At 48 hours after infection, supernatants from each well were harvested and frozen and thawed 3 times. To determine RGV titers, serial dilutions were performed on supernatants of serum-free medium and cells were titered on EPC. Each dilution was tested in triplicate. Data are represented as mean±S.E. Differences between groups were analyzed using an ANOVA and Dunnett's multiple comparison tests.

Figure 3:
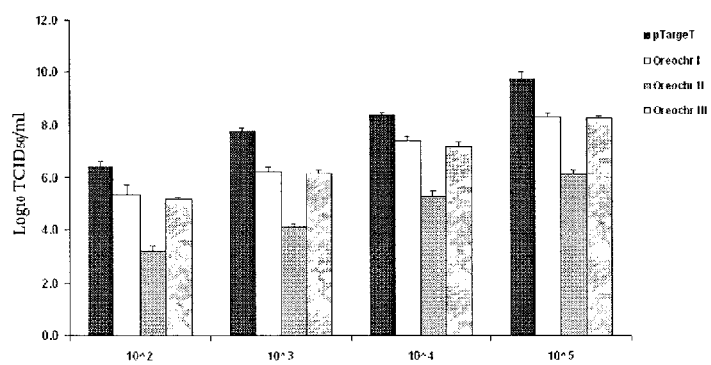
FIG. 3. Antiviral activity of the antimicrobial peptides Oreochromicin I, Oreochromicin II and Oreochromicin III. EPC (epithelioma papulosum cyprinid) cells seeded in 24-well plates were transfected for 24 h with 1 µg of pTargeT-Oreochromicin I, pTargeT-Oreochromicin II, pTargeT-Oreochromicin III or pTargeT as control. At 24 hours after transfection various concentrations of Rana grylio virus (RGV) ($10^5$ Infective Dose 50% of the virus (TCID50)/ml, $10^4$ TCID50/ml, $10^3$ TCID50/ml and $10^2$ TCID50/ml) were added, and 48 h later the culture supernatants were collected and viral titers were determined.

When cells were infected with $10^5$, $10^4$, $10^3$ and $10^2$ TCID50/ml of RGV, significant cytopathic effects were observed after 48 h of incubation in the cells transfected with the empty vector pTargeT compared with the rest of the cells expressing the antimicrobial peptides. Viral titers of cells expressing antimicrobial peptides were significantly lower than the titers of cells transfected with empty vector ($p<0.01$) (FIG. 3).

Example 7

Neutralization of LPS by Antimicrobial Peptides

Figure 4:
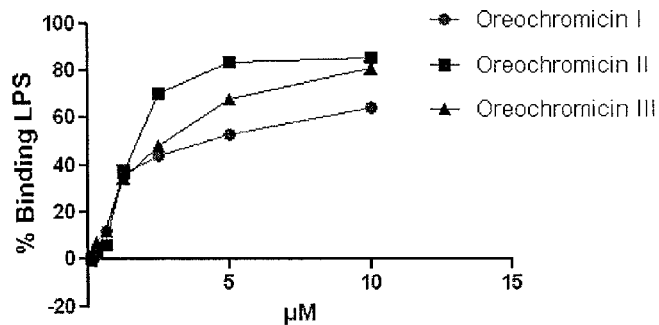
FIG. 4. Saturation curve of the antimicrobial peptides Oreochromicin I, Oreochromicin II, Oreochromicin III binding to lipopolysaccharide (LPS). The concentrations that produce 50% of peptide (Oreochromicina I, Oreochromicina II and Oreochromicina III) binding (EC50) were 1.23 μM, 1.41 μM and 2.99 μM, respectively.

Besides the antimicrobial activity and the possibility of increase disease resistance, we studied the ability of antimicrobial peptides of the present invention to neutralize LPS, by the Limulus amebocyte lysate (LAL) test. This assay detects the presence of free LPS unneutralized. Various concentrations of peptides were incubated with 0.5 EU/ml of LPS at 37° C. for 30 min. LPS alone was used as positive control of the assay. Subsequently, were added 100 µL of the mixture to equal volume of LAL reagent. The kinetic of the turbidity was measured using the equipment Tube Reader ATi-321 (Lab Kinetics, UK). As shown in FIG. 4, antimicrobial peptides of the present invention have the ability to neutralize LPS in a dose-dependent manner. The EC50 of peptides Oreochromicin I, Oreochromicin II and Oreochromicin III were 1.23 µM, 1.41 µM and 2.99 µM, respectively.

Example 8

Use of the Antimicrobial Peptides Oreochromicin I, Oreochromicin II and Oreochromicin III as Molecular Adjuvants Five experimental groups were formed of 12 tilapias (*O. niloticus*) each. The tilapias weighting 50 g each were injected intraperitoneally with PBS, cells of *A. hydrophila* inactivated with formalin and cells of *A. hydrophila* inactivated with formalin which was added each peptide at a dose of 1 µg/fish. Injections were performed on days 0 and 14. Blood was drawn from the caudal vein of the fish on days 0 and 21 and serum was stored at −20° C. until use.

The agglutinating antibody titers against *A. hydrophila* were determined by agglutination assay in 96-well plates. Serial dilutions of the serum samples (50 µL) were made in PBS and were added 50 µL of *A. hydrophila* cells inactivated with formalin ($4 \times 10^9$ cells/ml) to each well and mixed thoroughly. The plates were incubated overnight at room temperature, before examining the agglutination. The agglutinating antibody titers were expressed as the reciprocal of the highest serum dilution giving a positive agglutination.

Figure 5:
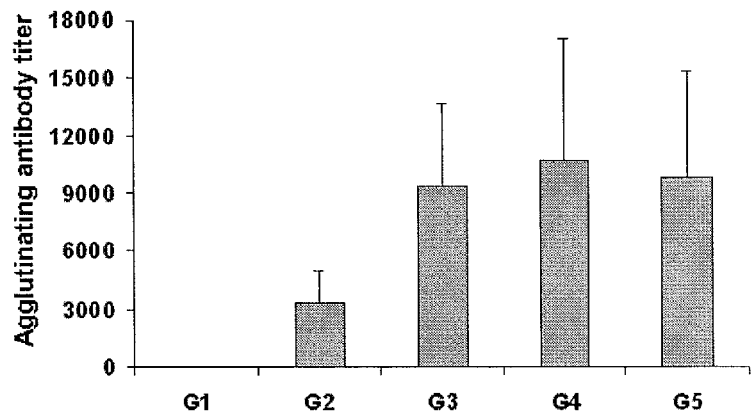
FIG. 5. Antibody titers against *Aeromonas hydrophila* in tilapias (n=12). Values represent the mean±standard error (SE).

The agglutinating antibody response against *A. hydrophila* is shown in FIG. 5. The observation of the average agglutinating antibody titers at week 3 after immunization show that the titers of the groups injected with inactivated bacteria cells co-administrated with antimicrobial peptides were superior to the groups injected with bacteria alone ($p<0.001$) or with PBS ($p<0.0001$). Moreover, there were significant differences in antibody titers between groups injected with PBS and injected with bacteria alone ($p<0.001$).

Example 9

Effect of Co-Immunization with Ovalbumin (OVA) and the Antimicrobial Peptides Oreochromicin I, Oreochromicin II and Oreochromicin III on the Humoral and Cellular Immune Response in Mice A) First Immunization Schedule We selected 24 BALB/c mice with a body weight of 20 g, which were separated into 4 test groups of 6 animals each. The negative control group (PBS/OVA) was intraperitoneally inoculated, on days 0 and 7, with a dose of 6 µg of OVA in 0.2 mL of PBS. The groups treated with peptides (PBS/OVA+peptide) were inoculated intraperitoneally on days 0 and 7 with a dose of 6 µg of OVA+0.5 µg of peptide in 0.2 mL of PBS. On day 15 of the immunization protocol, blood was drawn to animals and assessed total IgG titers.

Figure 6:
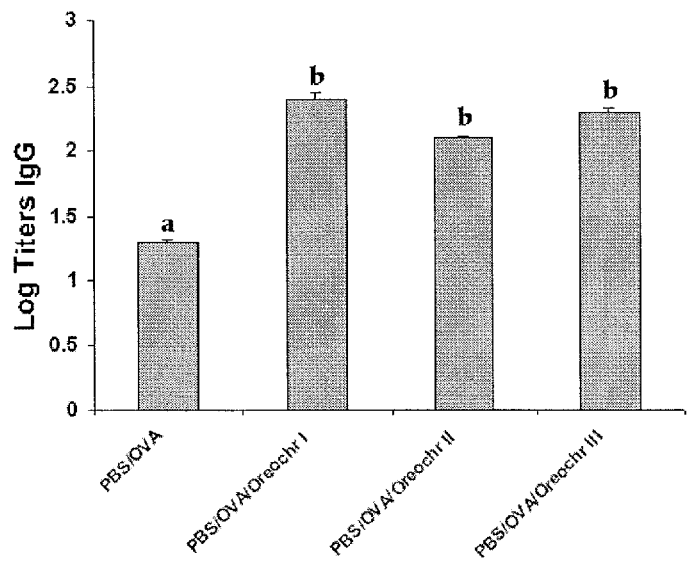
FIG. 6. Titers of total immunoglobulin G (IgG) induced in mice by the immunization with OVA co-administered with the peptides Oreochromicin I, Oreochromicin II and Oreochromicin III. Four experimental groups with 6 animals per group were established. The negative control group (phosphate buffered saline (PBS)/OVA) was inoculated intraperitoneally on day 0 and 7 with a dose of 6 μg of OVA in 0.2 mL of PBS. The groups that also received the peptides (PBS/OVA+peptide) were inoculated intraperitoneally on day 0 and 7, with a dose of 6 pg of OVA+0.5 μg of each peptide in 0.2 mL of PBS. Different letters indicate statistically significant differences. Values represent the mean±SE (n=6).

The FIG. 6 shows the total IgG titers induced by immunization of mice with OVA co-administered with each of the peptides. The animals in group PBS/OVA+peptide showed a specific total IgG titer against OVA statistically superior to the control group. This behavior was maintained for all peptides.

B) Second Immunization Schedule

64 BALB/c male mice were selected, which were 6 weeks old, and were separated into 8 experimental groups of 8 mice each. Administration of the immunogens was is conducted by intraperitoneal injection in a volume of 0.1 mL. The antimicrobial peptides were administered in equimolar amounts ($0.238 \times 10^{20}$ molecules and $2.38 \times 10^{20}$ molecules). The experimental groups were:

Group 1: Mice immunized with PBS.
Group 2: Mice immunized with OVA at a dose of 5 µg/animal.
Group 3: Mice immunized with OVA 5 µg/animal+Oreochromicin I at a dose of 0.1 µg/animal, equivalent to $0.238 \times 10^{20}$ molecules/animal.
Group 4: Mice immunized with OVA 5 µg/animal+Oreochromicin I at a dose of 1 µg/animal, equivalent to $2.38 \times 10^{20}$ molecules/animal.
Group 5: Mice immunized with OVA 5 µg/animal+Oreochromicin II at a dose of 0.12 µg/animal, equivalent to $0.238 \times 10^{20}$ molecules/animal.
Group 6: Mice immunized with OVA 5 µg/animal+Oreochromicin II at a dose of 1.2 µg/animal, equivalent to $2.38 \times 10^{20}$ molecules/animal.
Group 7: Mice immunized with OVA 5 µg/animal+Oreochromicin III at a dose of 0.14 µg/animal, equivalent to $0.238 \times 10^{20}$ molecules/animal.
Group 8: Mice immunized with OVA 5 µg/animal+Oreochromicin III at a dose of 1.4 µg/animal, equivalent to $2.38 \times 10^{20}$ molecules/animal.

Animals were immunized on days 0 and 14, and blood extractions were performed on days 0, 14 and 21. The serums of animals were used for determination of specific antibody titers (total IgG, IgG1 and IgG2a). At 59 days from the beginning of the experiment was extracted the spleen from the mice to determine the cellular immune response against the antigen OVA. The spleen was extracted under aseptic conditions and the splenocytes were isolated and were seeded $2.5 \times 10^5$ cells, at a cell concentration of $2 \times 10^6$ cells/mL in 96-well round bottom plate. Cells were stimulated with Concanavalin A (5 µg/ml) or OVA (10 µg/mL) and incubated at 37° C., 5% $CO_2$ for 4 days. Culture supernatants were collected and used for analysis of the levels of interleukin-4 and interferon-γ by ELISA.

Figure 7:
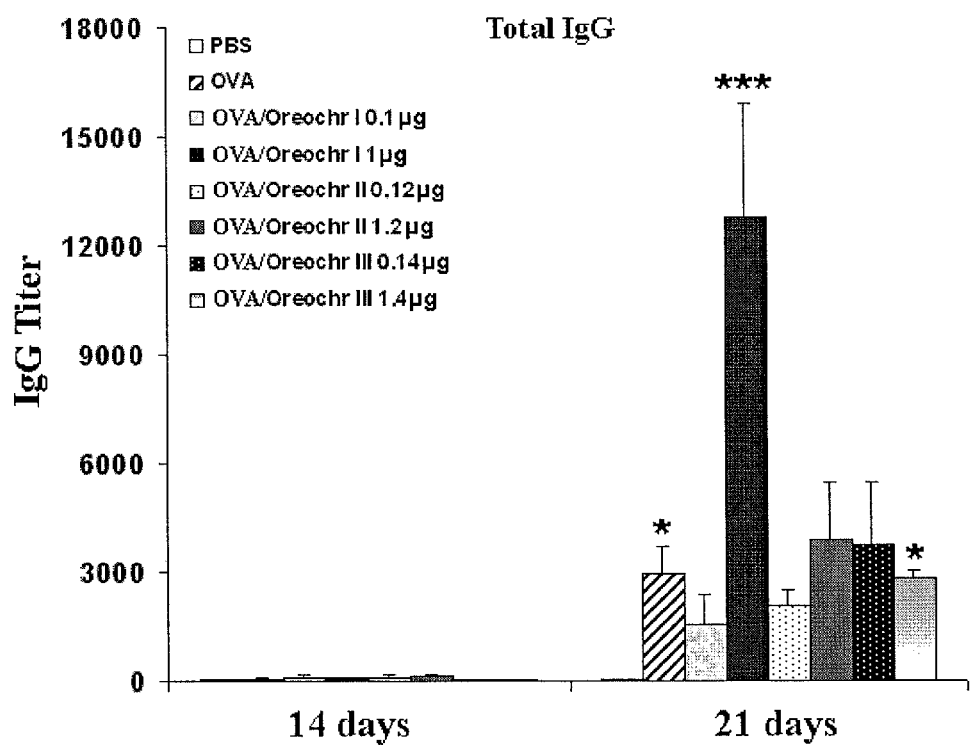
FIG. 7. Titers of total immunoglobulin G (IgG) (A), IgG1 and IgG2a (B) induced in mice by immunization with OVA co-administered with the peptides Oreochromicin I, Oreochromicin II and Oreochromicin III. Male Balb/c mice (8/group) were immunized by intraperitoneal injection on days 0 and 14 with OVA alone (5 μg/animal) or in combination with peptides at the doses of $0.238 \times 10^{20}$ molecules/animal (equivalent to 0.1, 0.12 and 0.14 μg/animal for Oreochromicina I, II and III, respectively) and $2.38 \times 10^{20}$ molecules/animal (equivalent to 1, 1.2 and 1.4 μg/animal for Oreochromicina I, II and III, respectively). The negative control group was injected with 0.1 mL of PBS. The OVA-specific humoral immune response (total IgG) was tested at 14 and 21 days after the first immunization. IgG1 and IgG2a antibody titers were analyzed at 21 days after the first immunization. The OVA-specific antibody titers were determined by ELISA. (A) Total IgG titers. Bars represent the IgG titer standard error (n=8). Statistical analysis was performed using a Kruskal-Wallis test and the Dunn multiple comparison test. Asterisks represent significant differences with the PBS group (* indicates $p<0.05$, *** indicates $p<0.001$). (B) IgG1 and IgG2a titers. Bars represent the antibody titer±standard error (n=8). Statistical analysis was performed using Mann Whitney test (*denotes $p<0.05$).
Figure 7:
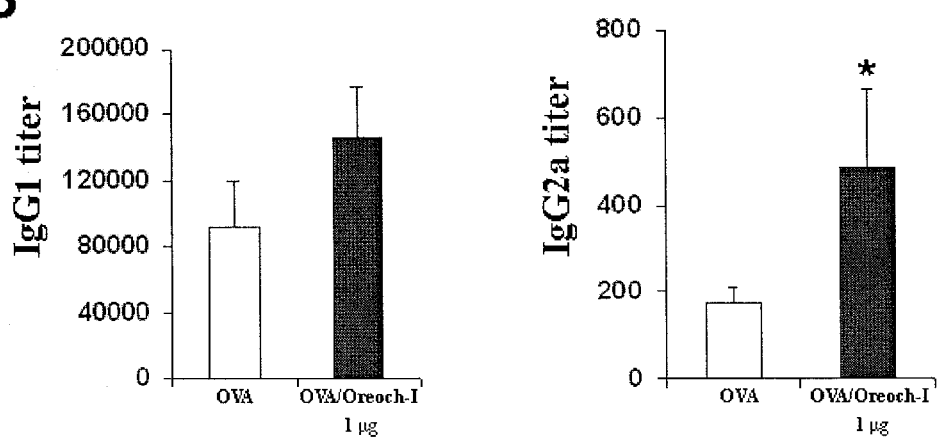

The FIGS. 7A and B show total IgG, IgG1 and IgG2a titers induced by immunization of mice with OVA co-administered with peptides Oreochromicin I, II and III. The animals in group PBS/OVA+Oreochromicin I, at a dose of 1 µg/animal showed a specific total IgG titer to OVA statistically superior to negative control group (p<0.001) (FIG. 7A). Animals in groups PBS/OVA and PBS/OVA+Oreochromicin III at a dose of 1.4 µg/animal also showed statistically significant differences in total IgG titers compared to the negative control group (p<0.05). Likewise, it was observed that the titers of specific IgG2a against OVA in the group immunized with PBS/OVA+Oreochromicin I, at a dose of 1 µg/animal were significantly greater than those observed in the group immunized with OVA alone 21 days after the first immunization (p<0.05) (FIG. 7B).

Figure 8:
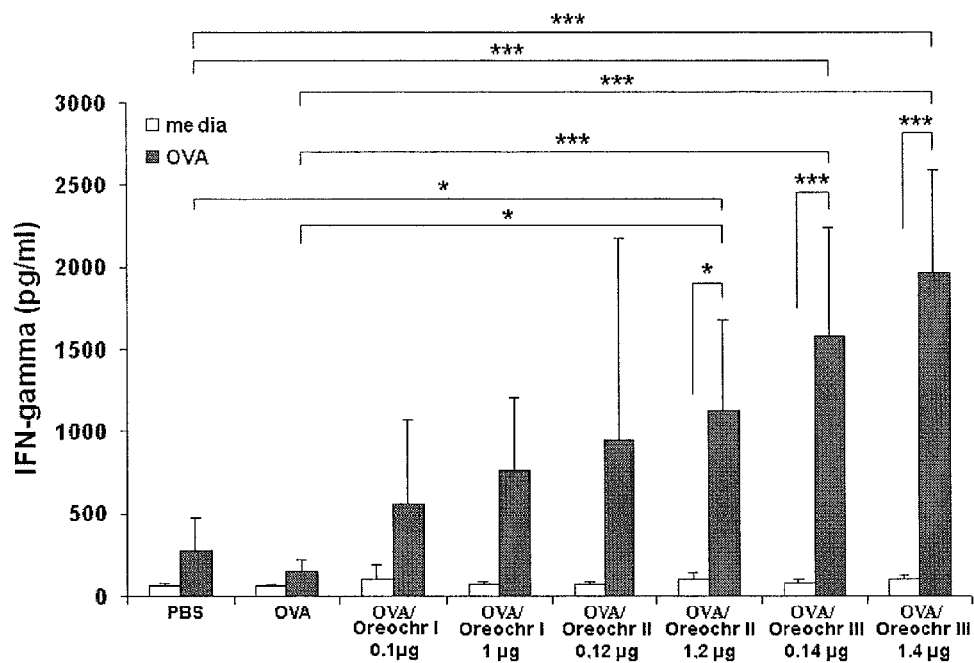
FIG. 8. IFN-γ secretion by spleen cells isolated from immunized animals. The Y axis shows the concentration of IFN-γ in the culture supernatant of splenocytes stimulated with OVA (10 μ/ml). Bars represent the concentration of IFN-γ±standard deviation (n=5). Statistical analysis of the data was performed by ANOVA test and Bonferroni's multiple comparison test (*: $p<0.05$, ***: $p<0.001$).

The culture supernatants of splenocytes stimulated with OVA from immunized animals were analyzed by ELISA to measure the concentration of IFN-γ and IL-4. As shown in FIG. 8, the highest levels of IFN-γ are obtained in animals immunized with OVA co-administered with the peptide Oreochromicin III in a dose dependent manner. These levels were significantly higher than the levels obtained in splenocytes from animals immunized with OVA or PBS alone (p<0.001). Furthermore, the levels of secretion of IFN-γ in animals immunized with OVA co-administered with the peptide Oreochromicin II at a dose of 1.2 µg/animal were significantly higher than the levels obtained in splenocytes from animals immunized with OVA or PBS alone (p<0.05) (FIG. 8). There was no IL-4 secretion in either group under the experimental conditions employed.

Example 10

Effect of Co-Immunization of the Antigen MY32 and the Peptide Oreochromicin I on the Humoral Immune Response in Tilapia To assess the ability of the peptide Oreochromicin I as molecular adjuvant in tilapia was used as vaccine antigen the protein MY32, previously known (Carpio et al. (2011) Vaccine 29: 2810-2820).

Six experimental groups were formed of 10 tilapias (*O. niloticus*) each with an s average weight of 45 g. The route of administration was intraperitoneal, the immunogen was applied in an injection volume of 0.3 mL. The experimental groups were:

Group 1: Fish immunized with PBS.
Group 2: Fish immunized with the protein MY32 at a dose of 1 µg/g of body weight.
Group 3: Fish immunized with the protein MY32 at a dose of 1 µg/g of body weight co-administrated with the peptide Oreochromicin I at a dose of 10 µg/fish.
Group 4: Fish immunized with the protein MY32 at a dose of 1 µg/g of body weight co-administrated with the peptide Oreochromicin I at a dose of 1 µg/fish, all adjuvanted in Montanide 888.
Group 5: Fish immunized with the protein MY32 at a dose of 1 µg/g of body weight co-administrated with the peptide Oreochromicin I at a dose of 10 µg/fish, all adjuvanted in Montanide 888.
Group 6: Fish immunized with the protein MY32 at a dose of 1 µg/g of body weight, adjuvanted in Montanide 888.

The animals were immunized on days 0 and 14, and blood extractions were performed on days 0, 14, 21 and 28. The serums of the animals were used for the determination of IgM specific antibody titers.

Figure 9:
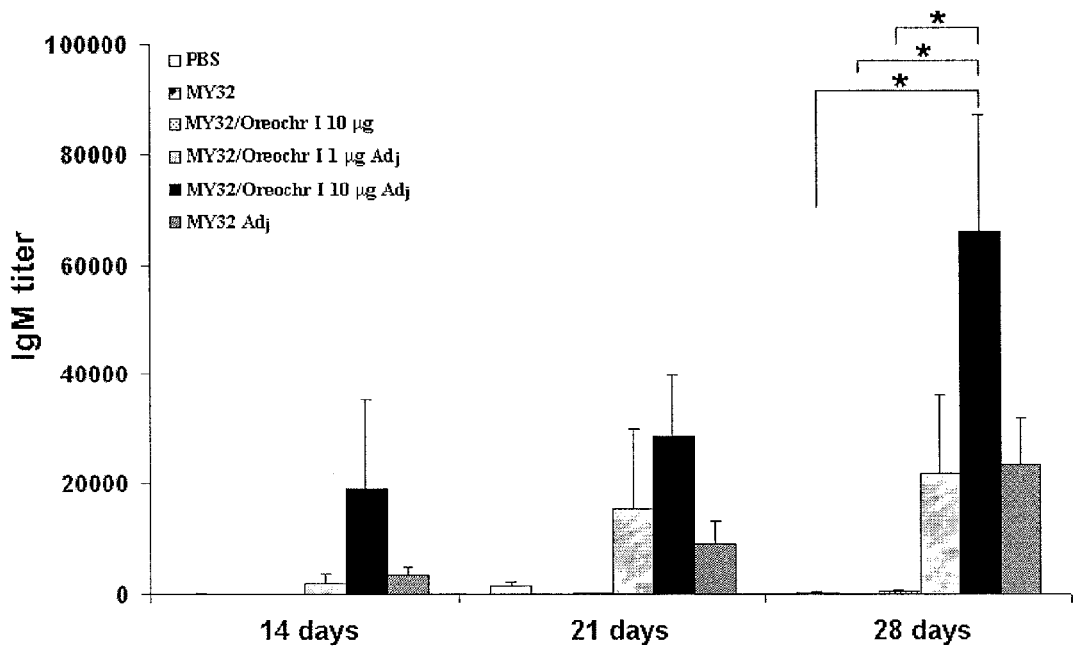
FIG. 9. IgM titers induced by immunization of tilapia (*O. niloticus*) with MY32 protein co-administered with the antimicrobial peptide Oreochromicin I. Fish (10 fish/group) were immunized by intraperitoneal injection on days 0 and 14. The negative control group was injected with 0.3 mL of PBS. The humoral immune response specific for MY32 was analyzed at 14, 21 and 28 days after the first immunization. The IgM antibody titers specific for MY32 were determined by ELISA. Bars represent the IgM titer±standard error (n=10). Statistical analysis of the data was performed by ANOVA and the Newman-Keuls multiple comparison test (*indicates $p<0.05$).

The FIG. 9 shows the IgM titers induced by immunization of fish with the MY32 antigen co-administered with the peptide Oreochromicin I. The animals in group MY32+ Oreochromicin I at a dose of 10 μg/animal, adjuvanted in Montanide 888, showed specific IgM titer against MY32 statistically superior to the groups immunized with PBS, MY32 and MY32 and co-administered with Oreochromicina I peptide at a dose of 10 μg/fish (p<0.05) (FIG. 9). No significant differences were observed among the rest of the experimental groups.

The invention claimed is:

1. A feed composition for the control of pathogens in fish, said composition comprising (i) feed suitable for fish and (ii) a peptide having a sequence identified as SEQ ID No. 1, SEQ ID No. 2 or SEQ ID No. 3, or an amino acid sequence having antimicrobial activity and at least 95% identity with SEQ ID No. 1, SEQ ID No. 2 or SEQ ID No. 3.

2. The composition according to claim 1 wherein the peptide is obtained by isolation from its natural source, by chemical synthesis or by recombinant DNA technology.

3. The feed composition accordingly to claim 1, wherein said peptide is present in an amount of between 50-750 μg/kg of feed.

4. A method for inhibiting infection by pathogens in living organisms, said method comprising administering an effective amount of a peptide comprising an amino acid sequence identified as SEQ ID No. 1, SEQ ID No. 2 or SEQ ID No. 3, or an amino acid sequence having antimicrobial activity and at least 95% identity with SEQ ID No. 1, SEQ ID No. 2 or SEQ ID No. 3 to said organism, wherein said pathogen is a bacterial, viral or fungal pathogen.

5. The method according to claim 4 wherein the peptide is administered therapeutically.

6. The method according to claim 4 wherein the peptide is administered to mammals and aquatic organisms.

7. The method according to claim 6 wherein the peptide is administered to fish.

8. The method according to claim 7 wherein the peptide is administered by periodic injections at concentrations between 0.1 and 10 μg of peptide/fish, by immersion baths at a concentration between 0.01 and 0.1 mg of peptide/liter of water, or as a feed additive at a concentration of about 50-750 μg of peptide/kg of feed.

9. An vaccine composition that comprises (i) a peptide comprising an amino acid sequence identified as SEQ ID No. 1, SEQ ID No. 2 or SEQ ID No. 3, or an amino acid sequence having antimicrobial activity and at least 95% identity with SEQ ID No. 1, SEQ ID No. 2 or SEQ ID No. 3, as a molecular adjuvant, and (ii) a vaccine antigen.

10. The vaccine composition according to claim 9, further comprising a second adjuvant.

11. The vaccine composition according to claim 10, wherein said second adjuvant is a water in oil emulsion.

12. A method for enhancing the immune response against a vaccine antigen in an organism, said method comprising administering an effective amount of a peptide comprising an amino acid sequence identified as SEQ ID No. 1, SEQ ID No. 2 or SEQ ID No. 3 or an amino acid sequence having antimicrobial activity and at least 95% identity with SEQ ID No. 1, SEQ ID No. 2 or SEQ ID No. 3, as a molecular adjuvant in a vaccine to said organism.

* * * * *